United States Patent
Cole et al.

(10) Patent No.: US 10,022,217 B2
(45) Date of Patent: *Jul. 17, 2018

(54) INTRAOCULAR LENS INSERTION DEVICE

(71) Applicant: Abbott Medical Optics Inc., Santa Ana, CA (US)

(72) Inventors: Mark S. Cole, Trabuco Canyon, CA (US); Can B. Hu, Irvine, CA (US); Kevin R. Springer, Santa Ana, CA (US)

(73) Assignee: JOHNSON & JOHNSON SURGICAL VISION, INC., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/950,278

(22) Filed: Nov. 24, 2015

(65) Prior Publication Data

US 2016/0081795 A1    Mar. 24, 2016

Related U.S. Application Data

(63) Continuation of application No. 14/198,925, filed on Mar. 6, 2014, now Pat. No. 9,198,754, which is a
(Continued)

(51) Int. Cl.
*A61F 2/16* (2006.01)
*A61L 31/04* (2006.01)
(Continued)

(52) U.S. Cl.
CPC .......... *A61F 2/1675* (2013.01); *A61F 2/167* (2013.01); *A61F 2/1662* (2013.01);
(Continued)

(58) Field of Classification Search
CPC ..... A61F 2/1662; A61F 2/1675; A61F 2/1678
See application file for complete search history.

(56) References Cited

U.S. PATENT DOCUMENTS

| 4,897,079 A |   | 1/1990 | Zaleski et al. |
|---|---|---|---|
| 5,190,552 A | * | 3/1993 | Kelman ................ A61F 2/167 606/107 |

(Continued)

FOREIGN PATENT DOCUMENTS

| EP | 1972306 A1 | 9/2008 |
|---|---|---|
| WO | 2010059655 A1 | 5/2010 |

OTHER PUBLICATIONS

Pacifico, et al., 'Implantable Defibrillator Therapy: A Clinical Guide', 2002, Springer Science+Business Media, LLC, 1st edition, p. 50.*

(Continued)

*Primary Examiner* — Ashley Fishback
(74) *Attorney, Agent, or Firm* — Johnson & Johnson Surgical Vision, Inc.

(57) ABSTRACT

A cartridge for an intraocular lens insertion device is disclosed. An example cartridge may include an intraocular lens insertion cartridge body having a distal end and a proximal end and configured to receive an intraocular lens for insertion into a patient's eye through an incision; the intraocular lens insertion cartridge body having an inner surface comprising at least one polymeric material having a hardness greater than about 50D and an elongation at break greater than about 150%; the inner surface of the intraocular lens insertion cartridge body defining an at least partially tapering insertion pathway disposed within the intraocular lens insertion cartridge body and extending from the proximal end to the distal end of the intraocular lens insertion cartridge body.

12 Claims, 7 Drawing Sheets

Related U.S. Application Data continuation of application No. 12/753,762, filed on Apr. 2, 2010, now Pat. No. 8,696,682.

(51) Int. Cl.
*A61L 31/06* (2006.01)
*A61L 31/10* (2006.01)

(52) U.S. Cl.
CPC .......... *A61F 2/1678* (2013.01); *A61L 31/048* (2013.01); *A61L 31/06* (2013.01); *A61L 31/10* (2013.01)

(56) References Cited

U.S. PATENT DOCUMENTS

| | | | |
|---|---|---|---|
| 5,300,115 A | 4/1994 | Py | |
| 5,549,109 A * | 8/1996 | Samson | A61B 5/0422 600/381 |
| 6,605,093 B1 | 8/2003 | Blake | |
| 2002/0151904 A1* | 10/2002 | Feingold | A61F 2/1664 606/107 |
| 2004/0267359 A1 | 12/2004 | Makker et al. | |
| 2005/0222532 A1* | 10/2005 | Bertolero | A61M 25/10 604/4.01 |
| 2007/0005135 A1 | 1/2007 | Makker et al. | |
| 2008/0172033 A1* | 7/2008 | Keith | A61B 1/00154 604/506 |
| 2010/0125279 A1 | 5/2010 | Karakelle et al. | |

OTHER PUBLICATIONS

International Search Report and Written Opinion for Application No. PCT/US2011/029726, dated Sep. 22, 2011, 14 pages.

* cited by examiner

INTRAOCULAR LENS INSERTION DEVICE

RELATED APPLICATIONS

This application is a continuation application of, and claims priority to, U.S. application Ser. No. 14/198,925 filed on Mar. 6, 2014, which is a continuation application of, and claims priority to, U.S. application Ser. No. 12/753,762 filed on Apr. 2, 2010, both of which are hereby incorporated by reference in their entirety.

BACKGROUND

Intraocular lens inserters are devices designed to insert an intraocular lens (IOL) into the eye of a patient. Such lenses are surgical implants designed to augment or replace the natural lens of the eye, and are used to treat certain diseases of the eye. For example, the impairment of vision caused by cataracts is often treated by the surgical removal and replacement of the eye's lens. During such a surgery a small 1-4 mm incision is formed in the patient's eye. The surgeon then uses a tool, inserted into the eye through the incision, to emulsify (break up) and remove the eye's natural lens. Once removed an artificial intraocular lens is inserted in the eye. In order to insert the lens without enlarging the incision, lenses are employed which may be compressed or folded, and inserted through an incision, using a device designed for the purpose. During insertion, significant forces may be applied to both the insertion device and the lens, which may lead to lens damage, insertion failures, and possibly patient injury. Some embodiments of the present invention provide insertion devices capable of inserting an intraocular lens safely and easily, and with a low risk of damaging the lens during insertion.

SUMMARY

Some example embodiments of the present invention may provide a cartridge for an intraocular lens insertion device having an intraocular lens insertion cartridge body further including a distal end and a proximal end and configured to receive an intraocular lens for insertion into a patient's eye through an incision. The intraocular lens insertion cartridge body can have an inner surface formed of at least one polymeric material selected from the group consisting of polyurethane, acrylic butyldiene styrene, styrene butyldiene styrene, high impact polystyrene, a polyester polymer, polymeric blends or copolymers thereof. The at least one polymeric material may have a hardness greater than about 50 D and an elongation at break greater than about 150%. The inner surface of the intraocular lens insertion cartridge body defines an at least partially tapering insertion pathway disposed within the intraocular lens insertion cartridge body and extending from the proximal end to the distal end of the intraocular lens insertion cartridge body.

Further example embodiments provide an intraocular lens insertion device having an elongated device body with a proximal end and a distal end and configured to receive an intraocular lens for insertion into a patient's eye through an incision. The elongated device body can have an inner wall, a portion of which comprises at least one polymeric material selected from the group consisting of polyurethane, acrylic butyldiene styrene, styrene butyldiene, high impact polystyrene, a polyester, polymeric blends or copolymers thereof, wherein the at least one polymeric material having a hardness greater than about 50 D and an elongation at break greater than about 150%. The intraocular lens insertion device further includes an at least partially tapering insertion pathway defined by the inner wall and formed within the device body, the pathway having a distal opening at the distal end. The intraocular lens insertion device further includes a plunger configured to traverse through at least a portion of the insertion pathway.

In some embodiments, the polymeric materials described herein have a minimum tensile strength of about 1000 psi. For example, the polymeric material can be a polyurethane with a hardness between about 50 D and about 85 D, an aromatic polyurethane with a hardness of between about 55 D and about 75 D or an aliphatic polyurethane with a hardness between about 60 D and about 72 D.

The polymeric material, in further example embodiments, is sufficiently lubricious to allow the intraocular lens to pass through the insertion pathway undamaged without a lubricious coating.

In one embodiment, the external diameter of the distal end of the cartridge body is about 4 mm or less, or in other embodiments, about 2 mm or less.

In other embodiments, the intraocular lens insertion cartridge body is formed of a single unitary piece of polyurethane having a hardness between about 50 D and about 85 D. The intraocular lens insertion cartridge body can also be formed of at least two distinct materials, one of which is a polyurethane having a hardness between about 50 D and about 85 D. Even further, in another embodiment, the at least two distinct materials are joined using a comolding process (e.g. coinjection and/or coextrusion).

In some embodiments, at least a portion of the inserter or the cartridges described herein comprise a hydrophilic polymeric material. The hydrophilic polymeric material may include, but is not limited to, one or more of the following: hydrophilic polyurethane, polyvinylpyrrolidone, polyacrylic acid, polyacrylamides, polyhydroxyethyl methacrylate, and/or hyaluronan. In some embodiments, the hydrophilic polymeric material is disposed on the inner surface along a distal portion of the insertion pathway or is disposed on the inner surface along the entire insertion pathway.

BRIEF DESCRIPTION OF THE DRAWINGS

The present invention will be more readily understood from a detailed description of example embodiments taken in conjunction with the following figures.

DETAILED DESCRIPTION

Example embodiments of the present invention may provide an insertion device designed to insert an intraocular lens (IOL) into an eye. As explained above, some medical conditions require the surgical replacement or augmentation of the eye's natural lens. Such procedures involve the insertion of an IOL into the eye through a small incision. In order to perform such procedures while minimizing the trauma caused to the treated eye, incisions between 1-4 mm (preferably less than 2 mm) may be employed. Such incisions are typically significantly smaller than the IOL itself. Therefore, in order to insert the IOL into the eye, it may be compressed or folded during the insertion process. After insertion the IOL may then naturally expand within the eye and may be positioned as needed by the surgeon.

In order to compress or fold the IOL, and insert it through the small incision, example embodiments of the present invention may provide an insertion device. Such an insertion device may allow an IOL to be loaded in a chamber, and may provide a mechanism which forces the IOL through an opening of appropriate size. For example, some such devices may employ a tapering tube or cartridge, through which the IOL is inserted. Using such a device, the IOL may first be loaded into a wide chamber or opening into the device (or may be preloaded). Loading may be a relatively simple process, as the chamber or opening may be large enough to easily hold the IOL without significantly compressing or deforming the IOL. The IOL may then be moved through a tapering tube. As the IOL travels through the tube, the diameter of the tube may decrease, compressing the IOL until it is deformed into a shape small enough for insertion.

It is noted, however, that as the IOL moves through such a tube, and the diameter of the tube decreases, both the IOL and the tube may experience larger and larger normal forces acting on it, and accordingly may also experience larger and larger frictional forces. Such forces may tend to strain the tube, deforming it as larger and larger forces are applied. Should the forces involved become too great, it is possible that the tube of the insertion device may crack, rupture, deform into a useless configuration, or otherwise be damaged. Should such damage occur during the insertion of an IOL, the insertion process itself may fail, possibly damaging the IOL, or even causing patient injury.

Because, the volume of the IOL being inserted is fixed for a particular lens design for a particular diopter, the forces experienced by both the IOL and the insertion tube tend to increase as the diameter of the insertion pathway is decreased. The smaller the insertion pathway is the more force that is required and applied on the IOL to achieve insertion of the IOL. In addition, in order to manufacture insertion devices having smaller inserter diameters, which may be used with smaller incisions, it may be necessary to reduce the thickness of the material used to form the tip of the insertion device. Accordingly, although it is desirable to reduce the final diameter of the insertion tube as much as possible, as smaller tubes require smaller incisions, decreasing the diameter of the insertion tube tends to result in both the application of greater forces, and in a thinner tube material less able to withstand those forces. Thus, the ability to create smaller diameter insertion tubes is limited by the properties of the material used to construct the tube.

In the past, insertion devices have used insertion pathways formed of polyolefins, polypropylene, or other polymeric materials, such as polycarbonate. These materials provide some desirable features. For instance, polyolefins are easily molded into the necessary form and have reasonable mechanical strength. However, it may not be possible, or desirable, to use these materials with inserter tubes having small diameters, as they are generally unable to withstand the forces encountered during the insertion processes.

Accordingly, example embodiments of the present invention may provide IOL insertion devices, cartridges, etc., having small diameter insertion pathways which are able to successfully withstand the application of significant forces while allowing for safe and reliable insertion.

In particular, some example embodiments of the present invention may provide insertion devices having an insertion pathway constructed of a polymer material which has sufficient toughness to withstand the insertion process. "Toughness" as used throughout this application is intended to have the meaning commonly assigned to it in the material sciences. In that context, toughness measures a material's ability to absorb energy (e.g., stretch) without breaking. This can be illustrated as the area under a stress-strain curve as demonstrated in FIG. 6.

The materials commonly used for IOL insertion pathways, generally do not have sufficient toughness to function at smaller diameters. Accordingly, while such materials may be successfully used in insertion devices employing relatively larger diameter insertion pathways, as the diameter of the insertion pathway is reduced, new materials are needed. Accordingly, some example embodiments of the present invention may provide insertion devices with insertion pathways constructed partially or entirely of polyurethane polymers; styrene related copolymers, such as but not limited to, acrylic butyldiene styrene (ABS), styrene butyldiene styrene (SBS), and/or high impact polystyrene (HIPS); polyester polymers; and polymeric blends or copolymers thereof. Such materials may have sufficient toughness to enable the creation of small diameter insertion devices, and may also maintain or introduce other beneficial properties.

It is noted that polyurethane polymers may have a number of different compositions. For instance, particular polyurethanes may be aromatic or aliphatic and may be hydrophilic or hydrophobic. Such polyurethanes may have different mechanical properties, such as but not limited to toughness characteristics, other physical properties, and other surface properties.

Further regarding physical properties of polymeric materials described herein whether they be solids, gels, fluids, liquids or the like, hydrophobic polymeric materials generally have toughness characteristics and hydrophilic polymeric materials generally have lubricious characteristics. These characteristics are by no means limiting, but exemplary polymeric materials described herein generally exhibit such characteristics.

The polymeric materials used to form at least a portion of the insertion pathway can have a characteristic toughness that allows >150% elongation or strain without damaging the polymer (e.g., cracking or ripping). In some embodiments, the elongation is between about 150% and about 500%, or between about 250% and 400%. Further, the polymeric materials have tensile strengths preferably >1000 psi. Again, in other embodiments, the tensile strength can be between about 1000 psi and about 10,000 psi, or about 5000 psi and 8000 psi. As such, the insertion pathways described herein can stretch well beyond their manufactured diameters without failure from damage of the polymer.

Even further, example embodiments of the present invention may provide IOL insertion devices having insertion pathways formed from hydrophilic or hydrophobic polymers with a hardness greater than about 50 D, preferably between about 50 D and about 85 D. In particular, some example embodiments may employ an aromatic polyurethane with a hardness of between about 55 D and about 75 D, for example the Pellethane, Tecothane, Texin, and Esthane families of aromatic polyurethane, while other example embodiments may employ aliphatic polyurethane with a hardness between about 60 D and about 72 D, for example Tecoflex.

It is also noted that the "D" numbers provided above are measures of hardness. Specifically, the numbers provided above indicate the Shore (Durometer) hardness of the material, which is basically a measure of the material's resistance to indentation. The numbers do not directly measure the material's toughness. However, polymeric materials are commonly identified by their Shore hardness, and the materials identified above have favorable toughness. As such, example embodiments of the present invention employing such materials may provide insertion devices having insertion pathways of relatively small diameter.

Figure 6:
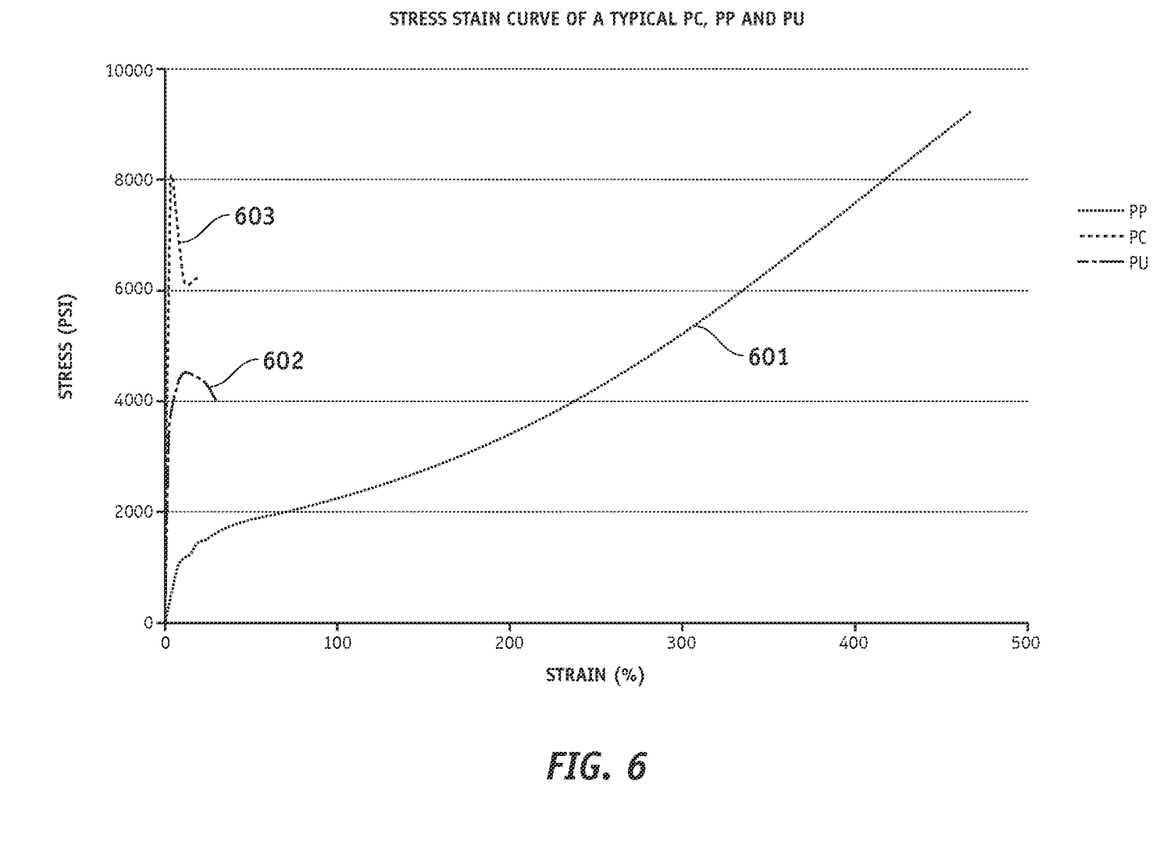
FIG. 6 illustrates a mechanical properties comparison (stress-strain curve) of polymeric materials of the present invention versus currently used materials.

Indeed, insertion tests performed using a variety of materials have demonstrated that the materials identified above are well-suited for use in insertion pathways. In particular, the materials identified above have mechanical properties which allow for the insertion of IOLs through smaller diameter pathways. In particular, the materials identified may be sufficiently tough to withstand the forces experienced during the insertion process. In addition, the materials allow for the construction of an insertion pathway which is also sufficiently rigid to support insertion. Testing also demonstrated that the traditional materials used in such insertion devices were largely unable to perform insertions in smaller diameter configurations. Rather, devices made of those materials either crack during insertion, as the forces become too great, the devices deform beyond usefulness, and/or the IOL becomes jammed inside the insertion pathway. FIG. 6 provides a stress-strain plot comparing the relative physical properties of a typical polyurethane 601 described herein against two other commonly used materials, polypropylene 602 and polycarbonate 603. To generate the plot an increasing force, stress, is applied to a sample of the material, and the amount the material deforms in response, strain, is measured and plotted, until the material breaks, at the end of the curve. The toughness of the material is represented by the area under the curve. As can be seen, the polyurethane material is very significantly tougher than the comparison materials.

In addition to the favorable toughness, and other structural properties, of the materials identified above, such materials have additional features which make them well-suited for use in smaller diameter insertion devices. For instance, as the diameter of the insertion pathway is decreased, the normal forces, and thus the frictional forces experienced by the IOL during insertion increase. These frictional forces tend to bind the IOL to the walls of the insertion device. Should they become too great, insertion may not be possible. Even where insertion is possible, the IOL may become damaged by these frictional forces, and the plunger forces needed to overcome them. For instance, the IOL may be scratched or torn during insertion, resulting in a failed procedure and possibly causing injury to the patient.

In order to alleviate the problems associated with increased frictional forces, lubricious materials may be used to form or coat the interior of the insertion pathway. Here, the materials described herein may themselves be sufficiently lubricious, or may be compatible with suitable lubricious ingredients in a lubricious coating mixture, to allow an IOL to be inserted through a small diameter. In fact, these materials may be more lubricious than many of the materials commonly used in IOL insertion devices, and may be more compatible with desirable lubricious coating mixtures.

For instance, inserter devices relying on polyolefin components, or components of other commonly used materials, often require lubrication to perform an insertion, as the material itself may not be sufficiently lubricious to deliver an IOL, unaided by external or internal lubricants. However, such materials have a number of properties which make lubrication difficult, which may require medical personnel to exercise a high degree of care, and which may ultimately result in a higher risk of damaged lenses.

For instance, one traditional way in which polyolefin components are lubricated, is by providing an internal lubricant. For example, glycerol monostearate may be blended into the polyolefin. The final material may be capable of inserting an IOL; however, such internal lubricants typically leach to the surface of the polyolefin structure over time, resulting in a limited shelf life. In turn, the limited shelf life may itself lead to damaged lenses and possibly patient injury, if practitioners are not attentive to the expiration dates of the components. In addition, the limited life also leads to higher costs for both providers and patients, as expired devices must be discarded.

External lubrication of the polyolefin components may also be problematic. For example, external lubrication with coatings of hydrophilic polymeric materials such as, but not limited to, hydrophilic polyurethane, polyvinylpyrrolidone, polyacrylic acid, polyacrylamides, polyhydroxyethyl methacrylate, and/or hyaluronan (materials which may be used to lubricate IOL insertion devices) may be difficult to accomplish effectively, as polyolefin is a hydrophobic material which is incompatible with the hydrophilic nature of lubricating materials, such as those described above. Again, the difficulty in providing a lubricious coating may ultimately result in higher costs, less ease of use, and a greater chance of lens damage and injury. However, the materials described herein may be both naturally more lubricious and also more compatible with coatings of hydrophilic polymeric materials which may be used to insert IOLs.

In addition, these materials may be sufficiently rigid to allow insertion, and they may also have properties which make them less likely to cause patient injury during use. For instance, during the insertion process, the tip of the insertion device is inserted into the patient's eye. If the device is too hard, it may cause trauma to the eye, such as but not limited to, breaking the capsular bag and debris in the eye. However, the materials described herein may be rigid enough for the initial insertion into an incision and may soften on contact with the eye's fluids. As such, insertion devices made from such materials may have a lower risk of causing significant trauma.

Figure 1A:
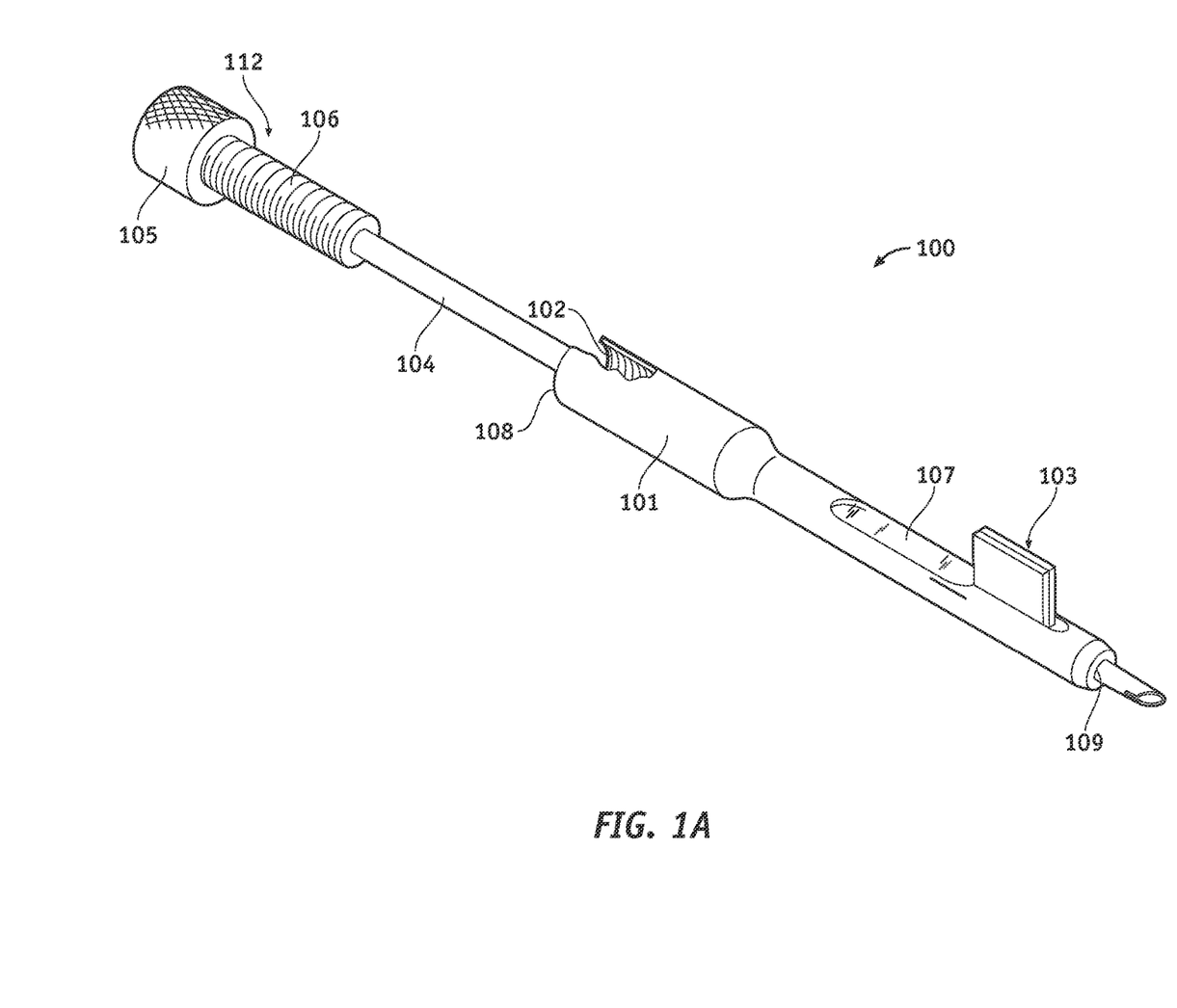
FIG. 1A illustrates an example inserter device in accordance with an example embodiment of the present invention.

An example insertion device is shown in FIG. 1A. As illustrated, the insertion device 100 may be generally shaped like a standard syringe. The device 100 may include a body 101 having an internal cavity 102 which may be sized and shaped to contain an IOL, a cartridge 103, or another similar structure. The device 100 may also include a plunger 112, designed to apply pressure on the IOL to push the IOL out of an end of the device 100 and into a patient's eye. For instance, some example devices 100 may include a plunger which may be traversable through the internal cavity 102 of the body 101. As the plunger is moved forward it may enter the area where the IOL is contained, e.g. the inside of a cartridge 103, or a loading area inside the internal cavity 102 itself. The plunger 112 may then make contact with the IOL and force it forward, through an insertion pathway.

The plunger itself may be constructed of any suitable material. For instance, it is noted that, because the plunger may come into direct contact with the IOL, it may be necessary to ensure that the plunger does not bind to the IOL. Further, the plunger itself may be required to traverse through the insertion pathway. Accordingly, the plunger may also experience increasing frictional forces, and may, therefore, need to be sufficiently lubricious and flexible to avoid any unnecessary stress. For instance, if the plunger were to experience frictional forces which become too great, a user may be required to apply significant force to perform the insertion, reducing the user's ability to do so accurately and with control. Accordingly, the plunger may be made of the materials described above, e.g. polyurethane or copolyester, or may be constructed of any other suitable material.

Plunger 112 of example devices 100 may also include a plunger rod 104. The plunger rod 104 may be formed of any suitable material. In addition, the plunger rod 104 may be connected to a thumb platform 105, or other structure, which may allow an operator to move the plunger forward by twisting and/or pushing the thumb platform 105 along a longitudinal axis of the device body 101 towards the distal end. Example embodiments may also provide a control mechanism. For instance, in the illustrated example, threads 106 may be provided on plunger 112, which may extend a portion of the length of the plunger rod 104, or its entire length. Matching threads may be provided on or inside the device body 101. Accordingly, when the threads 106 are engaged, the plunger rod 104 may be advanced forward in the manner of a screw, when the user twists the plunger rod 104. In this way, the plunger rod 104 may move forward at a controlled rate, preventing the possibility of a jerky insertion motion, or an overly forceful insertion. Any other control mechanism may also be provided, e.g. a damping system. Alternatively, the plunger rod 104 may be driven by a mechanical or electrical device. For instance, the plunger rod 104 may be connected to a motor designed to drive the plunger rod 104.

As explained, the insertion device body 101 may include an internal cavity 102. This internal cavity 102 may take the form of a bore extending longitudinally through the device body 101, giving the device body 101 substantially the form of a tube. The openings 108, 109 into the cavity may be located on both the distal and proximal end of the device body 101 (distal and proximal are used relative to a user of the device throughout the application, i.e. the IOL may be inserted into the eye through the distal end of the device). In addition, an opening 107 into the internal cavity 102 may be provided into which an IOL, a cartridge, etc., may be loaded. For example, as illustrated the device body 101 may include an opening 107 into which a cartridge 103 may be inserted, shaped to accept the cartridge 103 and to hold it in place. The opening 107 may be shaped to accommodate a cartridge 103. In other example devices, the IOL itself may be loaded directly into the internal cavity 102, in which case, the opening 107 may be shaped to accept the IOL, and may, e.g., include a door or covering allowing the opening 107 to be closed once the IOL is loaded. Further, in some embodiments the IOL may preloaded in the device 100. In such embodiments, no opening 107 need be included.

Further, in the case of a cartridge loaded into device body 101, the distal opening 109 may be shaped to allow the distal end of the cartridge 103 to extend out of the device body 101. For example, as illustrated, an insertion tip of the cartridge 103 extends out of a distal opening 109 formed in the distal end of the insertion device body 101. Of course, in other embodiments, the insertion tip need not be part of a cartridge 103; e.g. in some embodiments the insertion tip may be integrally formed with device body 101 of device 100, etc.

Figure 1B:
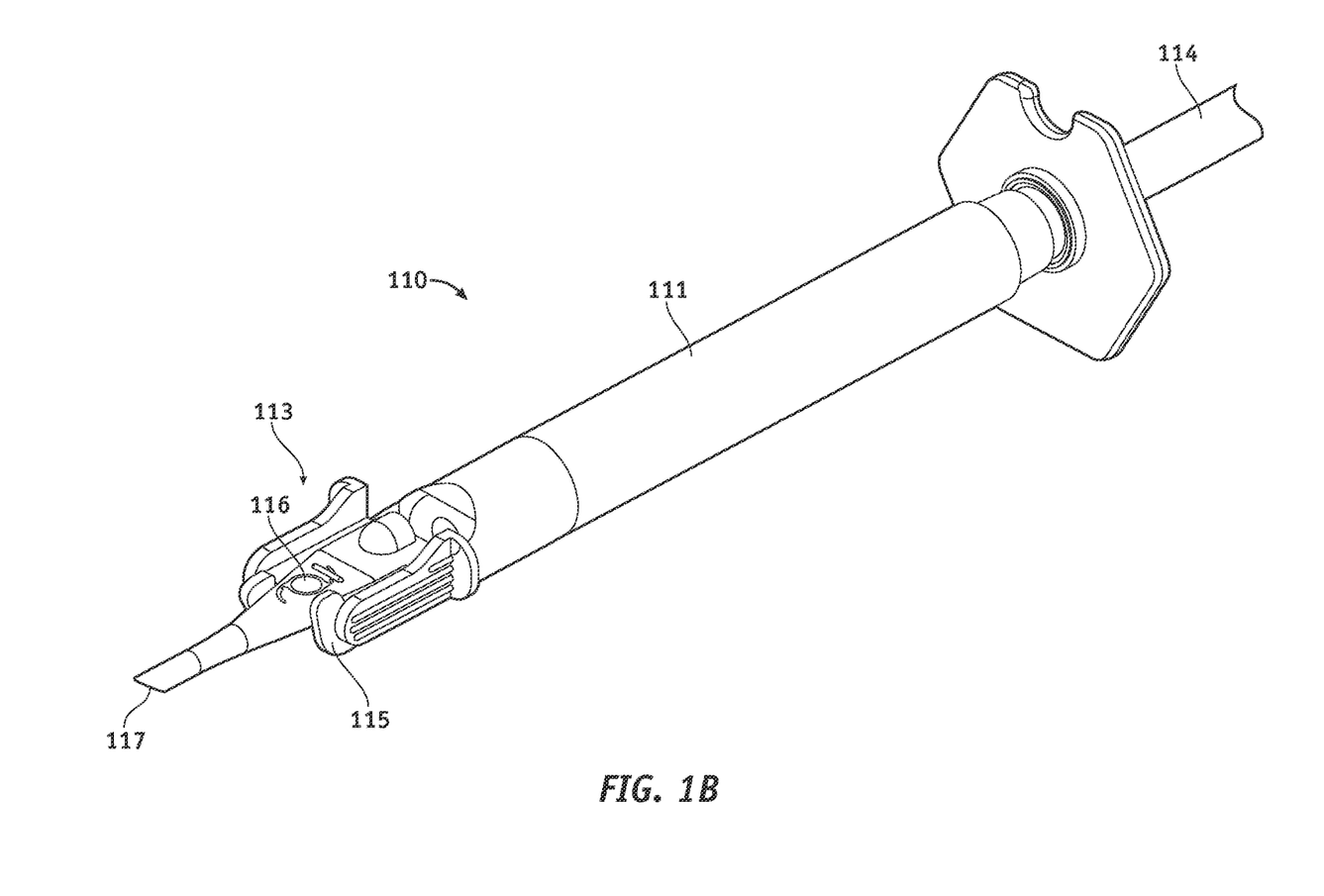
FIG. 1B illustrates an example inserter device in accordance with an example embodiment of the present invention.

Another example insertion device 110 is illustrated in FIG. 1B. The example insertion device 110 may again have a body 111, along with a plunger and plunger rod 114. In this example, the insertion device 110 may provide a mounting structure 115 allowing a cartridge 113 to be mounted at the distal end of the insertion device 110. For instance, as illustrated, the insertion device 110 may provide hook shaped protrusions shaped to accept the cartridge 113, although any other mounting structure may also be provided. The mounting structure 115 may be positioned at the distal end of the insertion device 110, adjacent to the plunger. During use the plunger may extend out of the body of the insertion device 110 and into the cartridge 113, making contact with the IOL 116, and pushing the IOL 116 through the insertion pathway and out the distal opening 117.

Figure 2:
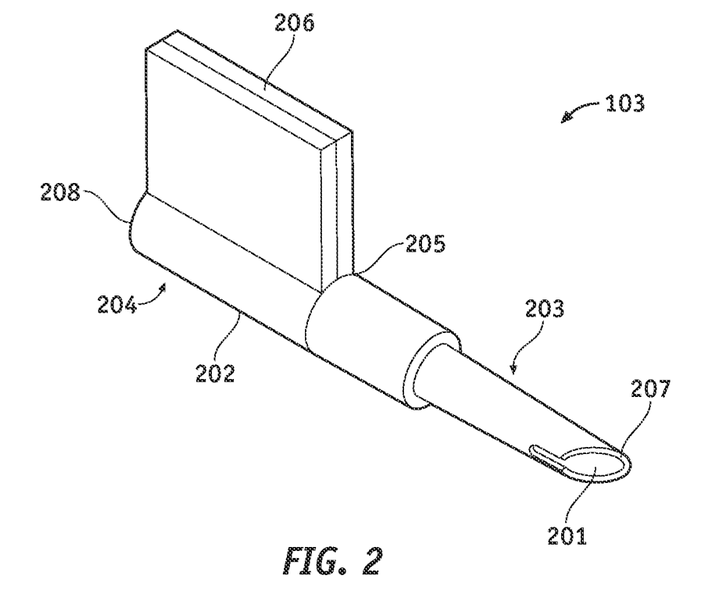
FIG. 2 illustrates an example cartridge in accordance with an example embodiment of the present invention.

As noted, example embodiments of the present invention may provide cartridges 103 for the insertion of IOLs. These cartridges 103 may be shaped to hold the IOL itself, and also to provide the pathway which the IOL traverses during the insertion process. An example cartridge 103 is illustrated in FIG. 2. As shown, the cartridge 103 may be shaped generally as a tube and may define an insertion pathway 201 through which an IOL may pass. The insertion pathway 201 may be at least partially tapering. For example, the insertion pathway 201 may taper from a wide diameter, near a proximal end of the cartridge, to a narrower diameter near a distal end of the cartridge. This taper may be formed such that, as the IOL is moved through the insertion pathway 201, toward the distal end, the IOL is compressed within the pathway 201. When the IOL reaches the distal end of the pathway 201 it will have been compressed to its smallest size, for insertion into the eye.

In order to ensure that the IOL is able to traverse the insertion pathway 201, without causing damage to the insertion pathway 201 and/or IOL, the insertion pathway should be able to withstand the application of the forces it will encounter during insertion. Accordingly, the insertion pathway 201 may be formed from materials of sufficient toughness to withstand those forces without cracking, rupturing, etc. In addition, in order to reduce the risk of damage to the IOL, and also reduce the insertion forces needed to perform the insertion, the insertion pathway 201 may be formed of sufficiently lubricious material, be coated with a lubricating material, or otherwise minimize the forces tending to bind the IOL to the interior wall of the pathway 201. These considerations are especially true for the distal end of the insertion pathway 201, because, as explained above, the tapering of the insertion pathway 201 means that normal forces experienced by the insertion pathway 201 and the IOL increase as the IOL is moved distally. Accordingly, in example embodiments of the present disclosure, the cartridge 103 may be formed of the materials described above. For instance, the cartridge 103 may be formed of aromatic or aliphatic, hydrophilic or hydrophobic polyurethane with a hardness between about 50 D and about 85 D, or from a copolyester. Further, some example cartridges may be formed of aromatic polyurethane with a hardness of about 55 D to about 85 D or aliphatic polyurethane with a hardness between about 60 D and about 72 D, etc., or other similar materials. For instance, in some example embodiments, the entire cartridge 103 may be integrally formed of such materials. For example the cartridge 103 may be formed as a single piece of such material using any suitable process, e.g. a molding process. In other example embodiments, the cartridge 103 may be formed of multiple materials. For instance, the insertion pathway 201 and/or the inner surface the insertion pathway 201 of the cartridge 103 may be formed of one of the materials described above, while the external portions of the cartridge 103, outer surface of insertion portion 203, and/or specific features such as hinges 202 or other structures, may be formed of another material, which may, for example, have other desirable mechanical properties, etc. Cartridges 103 formed from these materials may have sufficient toughness to safely withstand the insertion process, even when the diameter of the insertion pathway 201 is small, as described more fully below.

In addition, in order to counter the frictional forces which may be experienced during the insertion process, in some example embodiments a coating made of a hydrophilic polymeric material may be applied to the cartridge, or portions of the cartridge to provide additional lubricity. For example, in some embodiments a coating may comprise one or more hydrophilic polymeric materials, such as but not limited to, hydrophilic polyurethane, polyvinylpyrrolidone, polyacrylic acid, polyacrylamides, polyhydroxyethyl methacrylate, and/or hyaluronan, or the like, which may be applied to portions of the cartridge. As explained above, such coatings may be more compatible with the materials used to form the cartridge, and may therefore better adhere to the material of the cartridge. For instance, in some example embodiments, a coating may be applied to the cartridge along the insertion pathway 201

It is noted, however, that the materials and lubricants used in the cartridge 103 need not be applied uniformly along the insertion pathway 201, or the rest of the cartridge 103. For instance, although the insertion pathway 201 through which the IOL will travel must be formed of a material of sufficient toughness to allow for insertion, and must also be sufficiently lubricious to allow for easy and safe insertion, the forces experienced by the insertion pathway 201 and the IOL may not be the same along the entire pathway 201. Rather, as explained above, the insertion pathway 201 may taper from a larger diameter near the proximal end to a smaller diameter near the distal end. As the IOL traverses the insertion pathway 201, therefore, the forces experienced by both the insertion pathway 201 and the IOL will tend to increase, as the interior walls of the cartridge 103 force the IOL to fit into a smaller and smaller space.

In some embodiments, a blend of lubricous materials can be used to coat at least a portion of the cartridge. For example, a blend of a polyvinylpyrrolidone with a high molecular weight polymer (e.g. polyurethane) may be used. The high molecular weight polymer can be hydrophobic or hydrophilic depending on the particular cartridge materials, IOL being inserted and desired lubricity of the blend itself. Exemplary lubricious blends include polyvinylpyrrolidone and urethane; and hyaluronan and urethane.

Accordingly, in some embodiments, the material forming the cartridge need not have the same physical properties throughout the length of the insertion pathway 201. Rather, the cartridge may be formed of a material having a somewhat lower toughness (or lubricity, etc.) near the proximal end of the cartridge, where the IOL will be largely in its natural state, and may be of a higher toughness (or lubricity, etc.) near the distal end of the cartridge, where the IOL will be in a more compressed state. For instance, the cartridge may be made as a single piece of the materials described above, may be made from a blend of the materials described, may be made using portions of both the materials described above and different materials, such as the traditional materials identified herein, etc. Such cartridges may be formed in any acceptable manner, e.g. may be formed as distinct pieces of material and joined together through a welding process, the application of an adhesive, etc., or may be formed as an integrated piece, e.g. using a blended material.

In addition, some example embodiments may utilize material formed using a comolding process. Using such a process, two or more materials (e.g. polymers) may be extruded and/or injected to form a single piece, and may allow for the use of materials having different physical properties. For instance, materials may be used having both sufficient toughness and other desirable properties. For instance, a polyurethane may be used having sufficient toughness, as described above, while another polyurethane may be used having desirable lubrication properties—e.g., a polyurethane formed using polyethylene glycol as the soft segment, as such polyurethanes are significantly lubricious and are also hydrophilic, allowing for the simple use of coatings such as those described above.

Further, some example embodiments may utilize material formed using a co-molding process. In this process, a first and second polymeric material are injected or poured into a mold. In some instances, the two polymeric materials are injected simultaneously; in other instances, one polymeric material can be injected or poured followed by the second polymeric material after an appropriate amount of time.

In one example co-molding embodiment, a first hydrophilic polymeric material is injected into a cartridge mold and forms the interior of the cartridge. An exemplary hydrophilic polymeric material is polyurethane or polyacrylic acid. Then, after injection of a hydrophilic polymeric material, a second hydrophobic polymeric material can be injected on top of the first hydrophilic material forming the outside of the cartridge. The two polymeric materials bond to one another during the molding process, thereby forming a unified cartridge.

In addition, similar considerations may also apply to the application of lubricants, or use of lubricious materials. For instance, in some example embodiments, only the distal portion of the insertion pathway may be coated or infused with a lubricating material such as a hydrophilic lubricant. In this way, the IOL may not be in contact with the lubricating material until necessary; reducing the likelihood that material will adhere to and streak the IOL. Similarly, the cartridge may be made of different materials, one material used for the proximal end of the cartridge, which may for example be of lower lubricity but be less likely to contaminate the IOL or may have more favorable structural properties, while the distal end may be formed of a different material with greater lubricity.

Returning to FIG. 2, the cartridge 103 may have a loading portion 204 and an insertion portion 203. The loading portion 204 may allow a user to easily load an IOL into the cartridge 103. For instance, the cartridge 103 may be hinged to open, allowing an IOL to be inserted into the insertion pathway 201. As illustrated in the figure, the cartridge 103 may have a seam 205 running longitudinally along a portion of its length (e.g. along the length of the loading portion 204). In addition, the cartridge 103 may have a hinge 202 disposed generally opposite the seam. The hinge 202 and the seam 205 may divide the cartridge, or a portion of the cartridge, into segments which may be spread apart by a user, giving the user access to the interior of the cartridge 103. When closed, these segments of the cartridge 103 may together define all, or a portion of the insertion pathway 201, e.g. the portion of the pathway 201 in which the IOL may initially be loaded. This portion of the insertion pathway 201 may have the largest diameter, and may be shaped so that the IOL may be easily inserted into the pathway 201. For example, as depicted, each segment may be one half of a tube divided along its longitudinal axis. The seam 205 may be formed in any reasonable manner. For instance, the cartridge 103 may simply be molded in an open or semi-open position such that a seam 205 is formed with the cartridge 103 is closed. Similarly, the hinge 202 may be of any reasonable type and may be of any number. For instance, the hinge 202 may be a living hinge formed as an integral part of the cartridge 103, e.g. during a molding process. Alternatively, the hinge 202 may be attached to the cartridge 103 after the cartridge 103 is formed, etc.

In addition, the cartridge 103 may include wings 206, grips, or other devices, which may allow a user to more easily open and handle the cartridge 103. For instance, as illustrated, some embodiments of the present invention may provide two wings 206 which may be shaped to allow a user to load an IOL into the cartridge 103. The wings 206 may be tab shaped (for instance shaped essentially as a rectangle) and one wing 206 may be attached to each portion of the cartridge 103 body. The wings 206 may be shaped to be easily manipulated by a user during the loading process. For instance, the wings 206 may be sufficiently large that the user is able to easily open and close the cartridge 103, without the need to touch the portion of the cartridge 103 which forms the insertion pathway 201 when closed, thus risking contamination. In some examples, the wings 206 may be attached to the body of the cartridge 103 adjacent to the seam 202. In addition, in some example embodiments, the wings 206 may be shaped to hold the cartridge 103 in place, when it is inserted into the device body 101.

As explained, the cartridge 103 may also have an insertion portion 203. This portion 203 of the cartridge 103 may be shaped generally as a tapering tube. As illustrated, the wide end of the insertion portion 203 may be attached to the loading portion 204 of the cartridge 103. For example, the two portions 203, 204 may be formed as a single integrated piece. Alternatively, they may be formed as distinct pieces, and attached together in any suitable manner, e.g., they may be welded, glued, attached with physical hardware etc. The interiors of the cartridge portions 203, 204 may form a continuous cavity, i.e. the insertion pathway 201, into which the IOL may be loaded, and through which it may be passed during the insertion process.

In addition, the insertion pathway 201 of the cartridge 103 may be open on both the proximal and distal end. For instance, a distal opening 207 of small diameter may be located at the distal end of the cartridge 103. This opening 207 may allow the IOL to pass out of the cartridge 103 and into a patient's eye during operation. In addition, the proximal end of the cartridge may also have an opening 208, which may allow a plunger to enter the cartridge 103 and to make contact with the IOL.

Because the toughness of the materials used herein may allow for the manufacture of example cartridges 103 having an insertion pathway 201 with an external diameter smaller than 4 mm, example embodiments of the present invention may provide cartridges 103 which have distal ends with external diameters of 4 mm or less. Indeed, some example cartridges 103 may have distal ends with external diameters of 2 mm or less. Such small diameters may require the use of materials having toughness properties like those of the materials described above in order to survive the insertion process.

Figure 3:
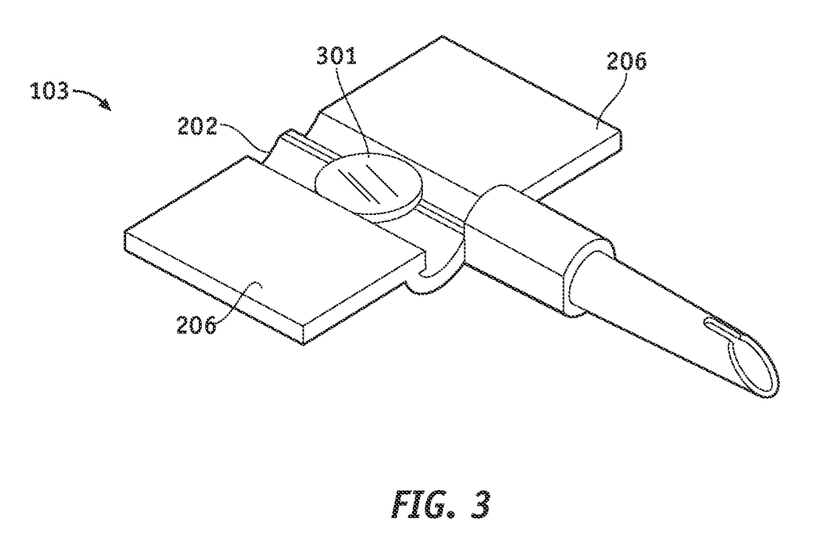
FIG. 3 illustrates an example cartridge in accordance with an example embodiment of the present invention.

FIG. 3 illustrates an example cartridge 103 in an open position. When opened, the inside of the insertion pathway 201 may be exposed to a user and may allow for easy loading of an IOL. As can be seen in the example, the cartridge 103 may open along a hinge 202 as described above. As illustrated, the opened cartridge 103 may have a size large enough to allow an IOL 301 to be placed within the opened insertion pathway 201. Thus, when the cartridge 103 is closed the IOL 301 will reside inside the insertion pathway 201.

Although some example embodiments may provide cartridges 103 which open along a longitudinal seam 205, it is to be understood that the present invention is not so limited and that other example embodiments extend to other kinds of cartridges, including cartridges which do not open, to inserter devices which do not use cartridges, and to other types of medical devices. For instance, some example embodiments may provide cartridges which may be preloaded with IOLs. Such cartridges need not open. Rather, the IOL may be installed in the cartridge during the manufacturing and/or assembly process. Such a cartridge may simply be formed of a single piece. In such embodiments, the proximal end of the cartridge may be formed with a cavity of sufficiently large diameter to contain the IOL for a significant period of time without causing a permanent deformation of the IOL. Again, such cartridges may be formed using the materials described above.

Figure 4:
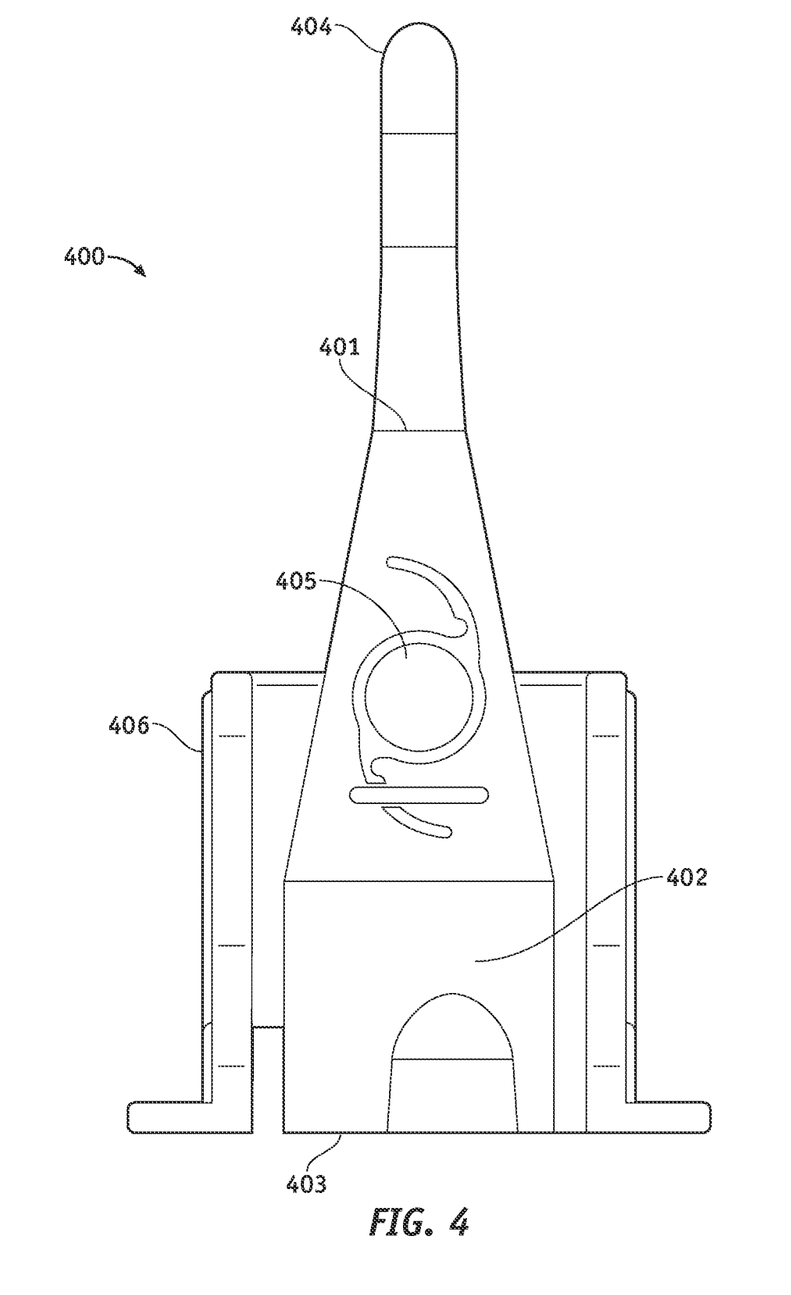
FIG. 4 illustrates an example cartridge in accordance with an example embodiment of the present invention.
Figure 5:
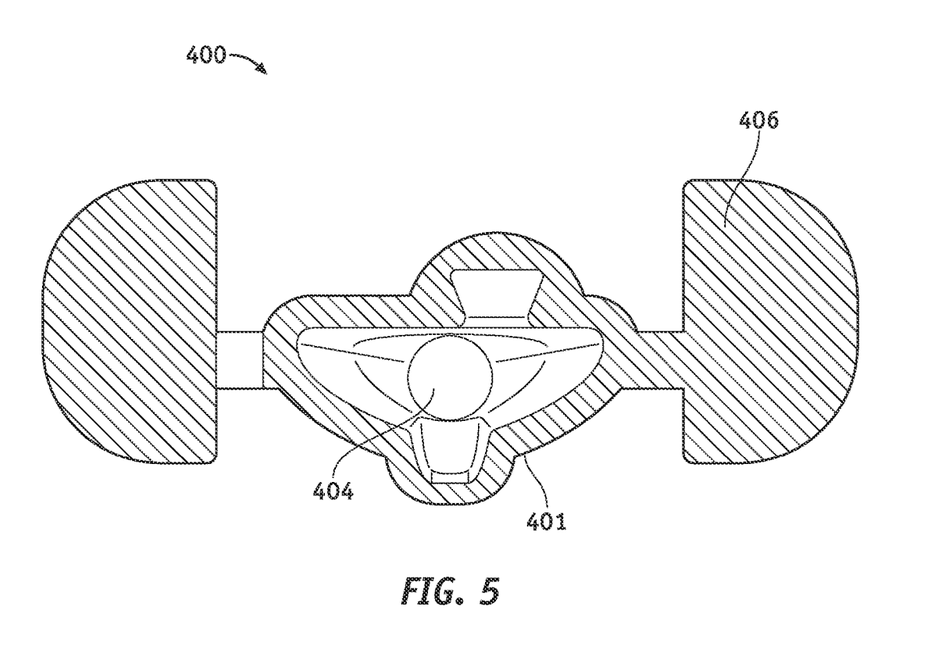
FIG. 5 illustrates an example cartridge in accordance with an example embodiment of the present invention.

FIGS. 4 and 5 illustrate another example cartridge 400 in accordance with example embodiments of the present invention. Here the illustrated cartridge 400 may be suitable for use with the example insertion device illustrated in FIG. 1A. As with the example cartridge described above, the cartridge 400 illustrated in FIGS. 4 and 5 may have a cartridge body 401, defining an insertion pathway 402, which may have both a proximal opening 403 and a distal opening 404. Again, the proximal opening 403 may be sized to allow a plunger to enter the insertion pathway 402 and traverse the IOL 405 through the insertion pathway 402. In addition, as shown in the figures, the IOL 405 may initially reside in a portion of the insertion pathway 402 which may have a diameter sufficient to allow the IOL 405 to rest substantially in an unfolded state. The IOL 405 may also reside adjacent to proximal opening 403 within an insertion body or insertion system. Similarly, the distal opening 404 of the insertion pathway 402 may be of a smaller diameter than the proximal opening 403. For instance, the distal opening 404 may be small enough to allow insertion of the IOL 405 into a small incision. For example, an external diameter of the cartridge 400 at the distal end may be 4 mm or less, and, in some examples, 2 mm or less. In order to accommodate the forces associated with such an opening 404, the example cartridge 400 may again be formed wholly or partly of the materials described herein.

As illustrated, the example cartridge 400 need not provide a hinge mechanism for loading an IOL 405, although a hinge or other opening mechanism may be provided. Rather, the cartridge 400 may either be preloaded with the IOL 405 or may allow for insertion of the IOL 405 through the proximal opening 403. In addition, the cartridge 400 may be designed to mount on the proximal end of an insertion device. For instance, the cartridge 400 may provide protrusions 406, which may be shaped to lock into a mounting structure disposed on an insertion device. Here the cartridge 400 may provide two wing-shaped protrusions 406 which may be shaped to lock into corresponding hook-shaped protrusions on the insertion device body.

Further, in some example embodiments, no cartridge may be employed. For instance, example embodiments may provide single use inserter devices. Such devices may include an insertion pathway formed within the body of the device itself. In such cases, the insertion pathway, or a portion of the insertion pathway, may be formed of the tough materials described herein. In such examples, the IOL may be preloaded into the body of the device, or the device may include an opening which may allow a user to load an IOL into the insertion pathway.

Example 1

IOL Delivery Test Using Cartridge Made of Various Polymeric Materials

Two types of delivery methods were used to evaluate the performance of cartridges made of different materials— hand delivery and "MARV" insertion force testing.

Hand Delivery

In the hand delivery test, four cartridges each made of a different material were tested and evaluated. The four materials tested were polypropylene (PD702), Pellethane 55 D (aromatic polyurethane), Lexan HPXS8R (polycarbonate), and Pellethane 75 D (aromatic polyurethane). The cartridge design was based on the cartridge 400 illustrated in FIGS. 4 and 5. The outer diameter of the insertion pathway of the cartridges was approximately 2.2 mm. The IOLs used to during the comparison testing were 30 diopter Tecnis® one-piece lenses (Abbott Medical Optics Inc.).

Prior to loading the IOL into the cartridge, each cartridge was visually inspected for cracks and that each cartridge had a full distal tip. Silicone fluid was added to the cartridges as a wetting agent and then the IOL was loaded into the cartridge. The cartridge containing the IOL was then loaded into the handpiece. The plunger was actuated to push the lens out of the cartridge and visual observations of the hand delivery were taken, which are set forth in Table 1 below.

TABLE 1

| Run | Cartridge Polymeric Material | IOL Status |
|---|---|---|
| 1 | Polypropylene (PD702) - Control | Jam |
| 2 | Pellethane 55D | Delivered IOL |
| 3 | Lexan HPXS8R | By pass, Jam |
| 4 | Pellethane 75D | Delivered IOL |

Table 1 shows that the 30 diopter IOL could not be delivered through cartridges made of polypropylene and polycarbonate. The IOL jammed inside the polypropylene cartridge making the IOL undeliverable. The IOL also jammed inside the polycarbonate cartridge making the IOL undeliverable and the plunger passed by the IOL inside of the cartridge without pushing the IOL. In contrast, cartridges made of Pellethane 55 D and 75 D delivered the IOL without damage to the IOL or to the cartridge.

MARV Force Testing

In the MARV Force testing, five cartridges made of different material were tested and evaluated. The five materials tested were polypropylene (PD702), Pellethane 65 D (aromatic polyurethane), Lexan HPXS8R (polycarbonate), Pellethane 75 D (aromatic polyurethane), and Tecoflex 65 D (aliphatic polyurethane). The cartridge design was based on the cartridge 400 illustrated in FIGS. 4 and 5. The outer diameter of the insertion pathway of the cartridges was approximately 2.2 mm.

Prior to loading the IOL into the cartridge, each cartridge was visually inspected for cracks and that each cartridge had a full distal tip. After inspection, silicone fluid was added to each of the cartridges followed by the IOL. The cartridge was then loaded into the MARV testing instrument. The MARV test measures the force applied to an inserter rod to push an IOL through a cartridge. Visual observations and insertion force measurements were taken, which are presented in Table 2 below.

| Run | Cartridge Polymeric Material | Cartridge Status | IOL Status | Peak (lbs) Stage 1 | Peak (lbs) Stage 2 |
|---|---|---|---|---|---|
| 1 | Polypropylene (PD702) - Control | Jam | Jam | 5.0. | 12.3 |
| 2 | Pellethane 65D | 0 | Pass | 2.6 | 5.2 |
| 3 | Lexan HPXS8R | TC | Pass | 4.2 | 12.1 |
| 4 | Pellethane 55D | 0 | Pass | 2.6 | 4.5 |
| 5 | Tecoflex 65D | 0 | Pass | 3.2 | 5.6 |

Table 2 shows the polymeric materials used to form the cartridge; the cartridge status after the IOL is inserted through the cartridge tip (0-2 scale, with 0 being the best and 2 being the worst, TC meaning the cartridge (tubing) cracked), IOL status after insertion, force at Stage 1, and force at Stage 2.

An IOL insertion test receiving a passing score was allowed up to a medium cartridge tube stretch, i.e. the cartridge was not heavily stretched or cracked. Stage 1 measurements recorded force data from the back of the cartridge to the tube dwells position and Stage 2 measurements recorded force data from the tube dwells position to the lower hard stop exiting the cartridge tip.

Based on the results demonstrated above, various polymeric materials used to form cartridges as described herein, assisted with a silicone fluid delivery aid, can deliver an IOL through the small insertion pathway without destroying the tube itself, the IOL, or potentially damaging the patient's eye. Based upon Table 2, the polyurethane cartridges delivered the IOL without damage to the IOL or to the cartridge and with a lower amount of force when compared to standard materials used for cartridges.

In the preceding specification, the present invention has been described with reference to specific example embodiments thereof. It will, however, be evident that various modifications and changes may be made thereunto without departing from the broader spirit and scope of the present invention. The description and drawings are accordingly to be regarded in an illustrative rather than restrictive sense.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. An intraocular lens insertion device, comprising:
an elongated device body having an insertion pathway defined between a proximal end and a distal opening at a distal end and configured to receive an intraocular lens for insertion into a patient's eye through an incision, wherein at least the distal end of the insertion pathway is a tapering tube formed of a polyurethane having a hardness between about 50 D and about 85 D, wherein the elongated device body is formed of at least two distinct materials, the polyurethane on the distal end of the insertion pathway and a second material on a proximal end thereof; and
a plunger configured to traverse through at least a portion of the insertion pathway.

2. The device of claim 1, wherein the polyurethane is an aromatic polyurethane with a hardness of between about 55 D and about 75 D.

3. The device of claim 1, wherein the polyurethane has a minimum tensile strength of about 1000 psi.

4. The device of claim 1, wherein the hardness is between about 55 D and about 75 D.

5. The device of claim 1, wherein the hardness is between about 60 D and about 72 D.

6. The device of claim 1, wherein the polyurethane is sufficiently lubricious to allow the intraocular lens to pass through the insertion pathway undamaged without a lubricious coating.

7. The device of claim 1, wherein an external diameter of a distal end of the tapering tube is about 4 mm or less.

8. The device of claim 1, wherein an external diameter of a distal end of the tapering tube is about 2 mm or less.

9. The device of claim 1, wherein the at least two distinct materials are joined using a comolding process.

10. The device of claim 1, wherein the comolding process is selected from the group consisting of coinjection and coextrusion.

11. The device of claim 1, further comprising:
a coating on an inner surface of the tapering tube comprising a hydrophilic polymeric material.

12. The device of claim 11, wherein the hydrophilic polymeric material is one or more selected from the group consisting of hydrophilic polyurethane, polyvinylpyrrolidone, polyacrylic acid, polyacrylamides, polyhydroxyethyl methacrylate, and hyaluronan.

* * * * *